United States Patent [19]

Minet et al.

[11] Patent Number: 4,804,797

[45] Date of Patent: Feb. 14, 1989

[54] PRODUCTION OF COMMODITY CHEMICALS FROM NATURAL GAS BY METHANE CHLORINATION

[75] Inventors: Ronald G. Minet, South Pasadena; Stanley C. Che, Los Alamitos, both of Calif.

[73] Assignee: Gas Research Institute, Chicago, Ill.

[21] Appl. No.: 88,240

[22] Filed: Aug. 24, 1987

[51] Int. Cl.$^4$ ................................................. C07C 2/00
[52] U.S. Cl. .................................... 585/500; 585/641; 585/642; 585/733; 585/943
[58] Field of Search ............... 585/500, 943, 641, 642, 585/733

[56] References Cited

U.S. PATENT DOCUMENTS

| 2,320,274 | 6/1941 | Gorin | 585/322 |
| 2,488,083 | 11/1949 | Gorin et al. | 585/642 |
| 4,051,193 | 9/1977 | Kurtz et al. | 585/657 |
| 4,199,533 | 4/1980 | Benson | 585/500 |
| 4,544,784 | 10/1985 | Sofranko et al. | 585/500 |

Primary Examiner—Curtis R. Davis
Attorney, Agent, or Firm—William W. Haefliger

[57] ABSTRACT

Natural gas components are converted to unsaturated hydrocarbons and hydrogen, as by a one-step process. The reaction products comprise a mixture containing hydrogen, acetylene, ethylene, propylene, $C_4$ species, aromatics, hydrogen chloride, etc. Acetylene and ethylene are separated from this mixture as main products; and hydrogen chloride is converted to chlorine for recycle.

12 Claims, 4 Drawing Sheets

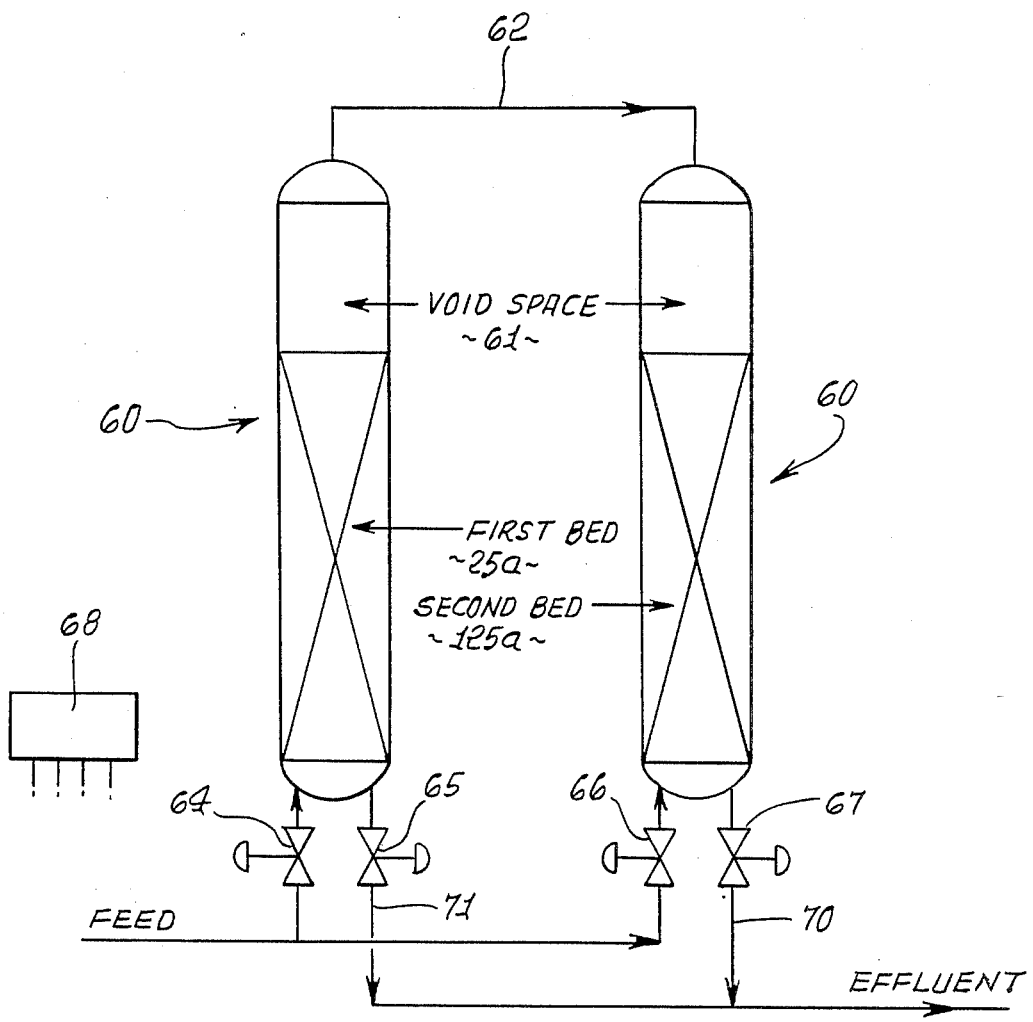

PRODUCTION OF COMMODITY CHEMICALS FROM NATURAL GAS BY METHANE CHLORINATION

BACKGROUND OF THE INVENTION

This invention relates generally to converting natural gas components into higher molecular weight hydrocarbons; more particularly it concerns an improved one-step process for such conversion, and employing methane chlorination.

In many areas of the world there are abundant supplies of natural gas which are widely distributed by pipeline systems. The composition of natural gas varies with the source but essentially it is made up of methane, (typically about 80% by weight), ethane, propane and other paraffinic hydrocarbons, along with small amounts of inorganic gases. Natural gas is mainly fuel.

For chemical stock consumption, current practices are mainly limited to the production of ammonia, hydrogen, methanol and carbon black. Natural gas has received limited use as a chemical feedstock principally because methane is the most stable of all hydrocarbons. To convert methane directly to other hydrocarbons involves both thermodynamic and kinetic barriers. For example, both net changes of enthalpy and Gibbs energy of the following reaction are unfavorable at all temperatures:

$$CH_4 \rightarrow 1/nC_nH_{2n+2} + (1-1/n)H_2 \quad (1)$$

Production of olefins and acetylenes involves even less favorable enthalpies of reaction. Their Gibbs energies of reaction become favorable only at temperatures above 1200° K. However, at these high temperatures, the route for the production of carbon and hydrogen is more favorable. Since methane is the most stable and has the strongest C—H bonds, any free radical process capable of producing "polymers" would tend to attack these polymer products more readily than to attack the parent methane. This process limits the yields attainable, kinetically.

Conversion of methane to ethylene, acetylene and hydrogen by using chlorine gas as a catalyst or a co-reactant has previously been described. For example, Gorin et al taught in U.S. Pat. No. 2,488,083 that methane can first be converted to methyl halide and then catalytically condensed to hydrocarbons having two or more carbon atoms to the molecule. Benson disclosed in U.S. Pat. No. 4,199,533 that ethane, ethylene and hydrogen can be produced from methane by reacting methane with chlorine at 700° C. or higher. U.S. Pat. No. 2,320,274 to Gorin describes production of benzene, ethylene and acetylene from two step reaction of methane and chloride, at temperatures between 600° and 1000° C., and residence times in excess of 10 seconds. If methane can be readily converted to basic petrochemical building blocks such as ethylene and acetylene, the use of natural gas as chemical feedstock is enhanced.

SUMMARY OF THE INVENTION

It is a major object of the invention to provide an improved, "one-step" process for efficiently converting natural gas components to unsaturated hydrocarbon and hydrogen. Basically, the method of the invention comprises reacting a mixture of chlorine and a gas comprising methane in a mole ratio of methane to chlorine of about 1.5:1 to 5:1 under conditions to provide a reaction pressure of about 3 atmospheres and a reaction temperature of at least about 900° C., and to form, as mixed reaction products, hydrogen chloride and a hydrocarbon or hydrocarbons selected from the group that includes, but not limited to, ethane, ethylene, acetylene, propylene, butadienes, acetylacetylene, benzene, alkylbenzenes, dialkylbenzenes, and heavy hydrocarbons having more than 10 carbon atoms, and hydrogen.

As will be seen, acetylene and ethylene are preferably separated from the mixture as principle products; hydrogen chloride in the mixture is removed and converted to chlorine, for recycling to the natural gas reaction or reactor; and acetylene is typically hydrogenated to ethylene or converted to vinyl chloride by reaction with hydrogen chloride.

Other objects include controlling the feed of methane and chlorine to achieve an exothermic reaction in the reaction zone to produce temperatures therein between 1,100° C. and 1,500° C.; providing an excess of methane in the reaction zone; separating hydrogen chloride from said reaction products, recovering chloride from the separated hydrogen chloride, and re-cycling the recovered chlorine to the methane chlorination reaction zone; and separating methane from the reaction product, and re-cycling the recovered methane to the methane chlorination reaction zone.

Further, and for heat conservation, the process is typically carried out in a reactor consisting of two sections of a regenerative heat exchange bed and a void space which is the reaction zone, and the said reaction zone is located between the two regenerative heat exchanger beds. The said regenerative heat exchanger beds consist of packing materials which are chemically inert with chlorine or chloride at temperatures higher than 800° C. As an example, high alumina ($Al_2O_3 > 90\%$ (weight)) can be used. The reactants, methane and chlorine, flow into the first regenerative heat exchanger bed which is either preheated or has absorbed heat from reaction products of the previous cycle, and wherein reactants are heated to the initial reaction temperature by absorbing heat from the packing material. The reactants then flow into the said void space wherein reaction products are exothermically produced and from which the reaction products flow to a second regenerative heat exchanger bed containing the same kind of materials as in the first regenerative heat exchanger bed. The reaction product mix releases heat to the regenerative bed material. In addition, the process typically includes reversing the flow of the methane and chlorine to the second regenerative heat exchanger bed for preheating the reactants to the desired reaction temperature, and then flowing the reactants to the void space wherein exothermic reaction takes place, and then flowing the reaction products to the first regenerative heat exchanger bed to transfer heat to the packing material therein.

These and other objects and advantages of the invention, as well as the details of an illustrative embodiment, will be more fully understood from the following specification and drawings, in which:

DRAWING DESCRIPTION

FIG. 1, is a process flow diagram;
FIG. 2 is a second process flow diagram;
FIG. 3 is a diagram of a methane chlorination reactor; and FIG. 4 is a diagram of a reactor couple.

DETAILED DESCRIPTION

Figure 1:
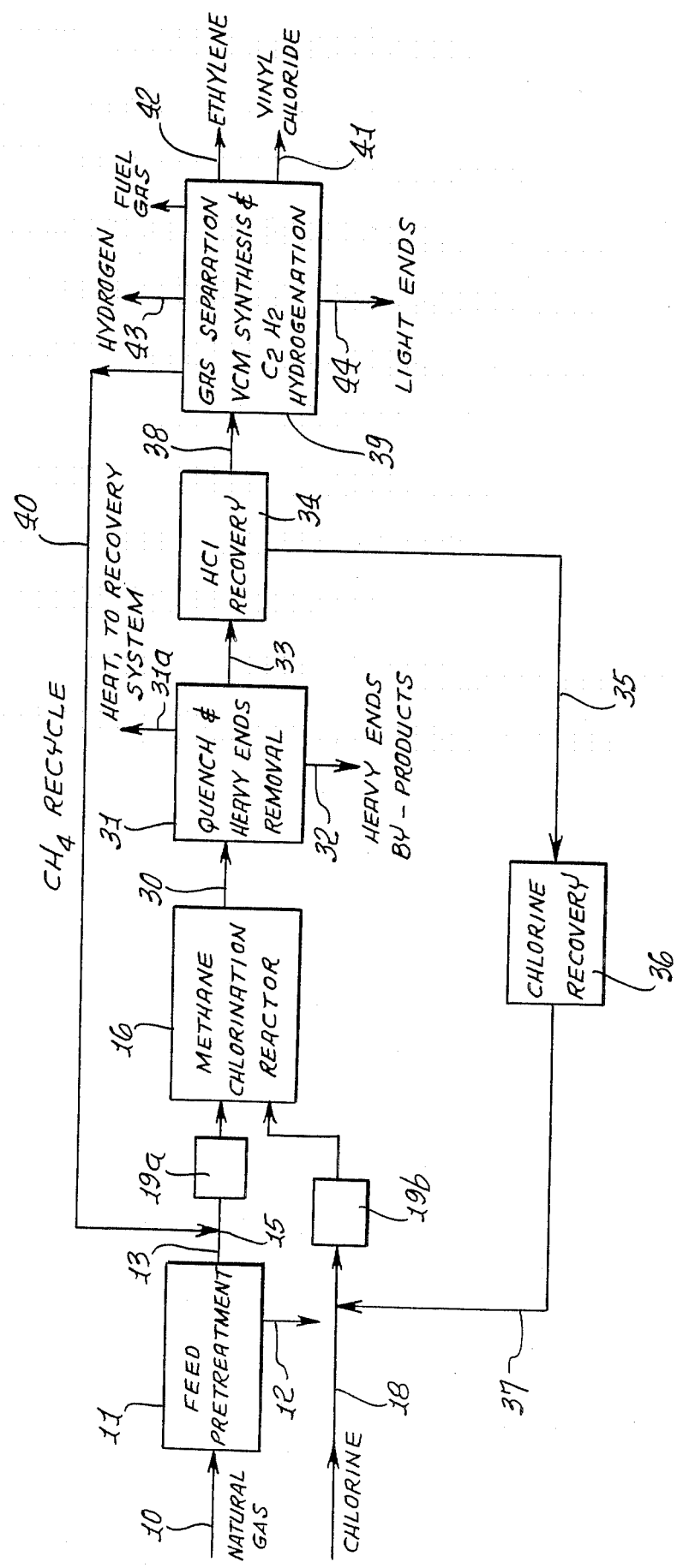
Figure 2:
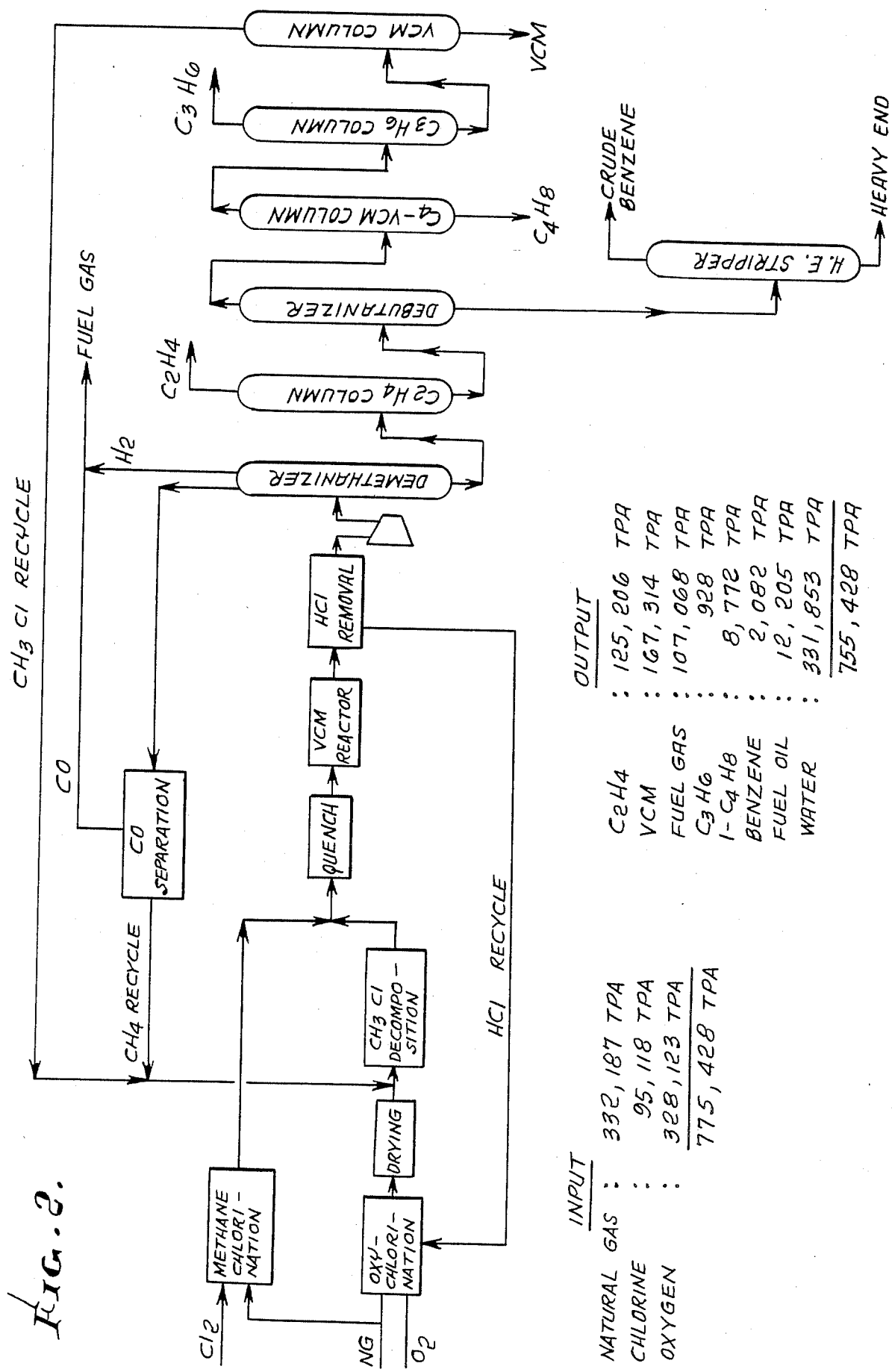

In FIG. 1, natural gas is fed at 10 to a feed pretreatment processor 11. In this regard, natural gas is widely distributed by pipelines, and contains about 80–99% (volume) of methane. The remainder can be various combinations of ethane, propane, butanes, pentanes, carbon dioxide, nitrogen and hydrogen sulfide or organic sulfide. Thus, the composition of natural gas in the pipeline is not uniform, and can vary significantly depending on the source of gas and the type of gas processing treatments that natural gas has received. Before the gas is delivered to the methane chlorination reactor 16, gas pretreatment may be required at 11 if the gas contains substantial amount of $CO_2$, $N_2$, sulfides and water. These are removed at 12. After such pretreatment, the fresh feed gas at 13 is combined at 15 with recycled methane 40 before feeding to the methane chlorination reactor 16.

Chlorine is also delivered at 18 to reactor 16, for reaction with methane. Typically, chlorine is delivered in liquid form to the user facility by railroad car. Normally, the purity is about 99.5% or higher. If moisture is present in such chlorine, drying may be required before the chlorine is fed to the methane chlorination reactor.

The methane chlorination reaction at 16 is precisely controlled for producing desired products. Both natural gas and chlorine are preheated to about 300° C. as at 19a and 19b prior to entering the reaction chamber. Preheating of these gases can be carried out separately on these two streams; alternatively, the gases can be mixed together before preheating. A third approach is to preheat the gases in stages, in which event natural gas and chlorine are preheated to predetermined temperature, separately. The partially preheated reactant gases, either separately or mixed together, enter the methane chlorination reactor 16 at about 300° C. The reactant gases absorb heat from the chemically inert packing material for further preheating to about 900° to 1200° C., and the preferred temperature is about 1180° C.

Figure 3:
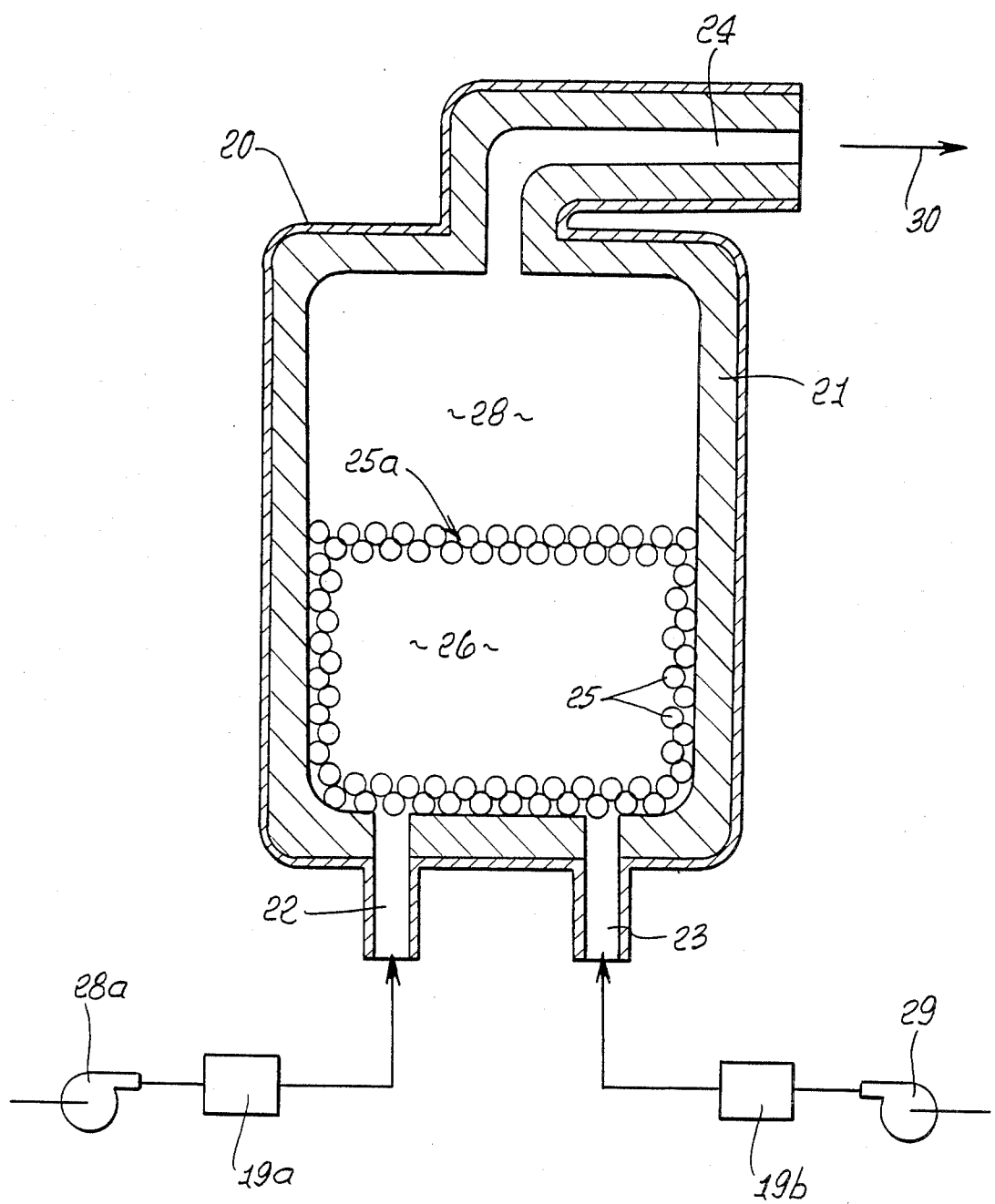

When the preheated reactants enter the reaction chamber, reaction takes place immediately. In terms of mechanistic steps, methane and chlorine from methyl chloride as the primary intermediate which decomposes spontaneously. Whereas the methyl chloride formation reaction is a strong exothermic reaction, decomposition of methyl chloride is an endothermic reaction. Along the reactor length, there is a temperature rise, initially. When the chlorine conversion reaches about 70%, the decomposition reaction of methyl chloride and secondary cracking reactions become dominant. Since these reactions are highly endothermic, the temperature profile decreases in the latter stage of the reactor. A typical reactor is shown at FIG. 3, and has an outer metal shell 20, a firebrick liner 21; inlets 22 and 23 for methane and chlorine, and a product gas outlet 24. Inert alumina balls 25 fill the reaction chamber 26, as shown, and define a regenerative heat exchanger bed. The void space 28 is one half of the reaction zone.

The methane chlorination reactor is operated at about 3 atmospheres. Higher operating pressure is undesirable because excessive production of heavier by-products occurs. Operating at atmospheric pressure is not desirable because the reactor effluent requires compression in the subsequent separation operation, such compression requiring excessive and uneconomic power consumption. The pumps 28a and 29 seen in FIG. 3 represent means for achieving such pressurization.

The initial temperature of the reaction zone 28 is an important controlling factor. The minimum temperature required is about 900° C. The preferred temperature is 1100° to 1500° C. At this temperature range, about 60 to 80% of the converted methane forms acetylene and ethylene, based on carbon selectivity. Control of such temperature may be achieved by controlling the feed rates of methane and chlorine.

Carbon selectivity is defined by the expression:

$$\frac{\text{wt of carbon in component}}{\text{wt of carbon from converted methane}} \times 100\% \qquad (2)$$

In this regard, methane must be in excess, in the reactor, to help produce ethylene. (At the stoichiometric ratio of methane to chlorine equal to 1:1, very little ethylene is produced). The required molar ratio range for methane to chlorine is 1.5:1 to 5:1. Too much excess methane results in an undesirably and uneconomic large methane recyle stream. The preferred ratio range is 1.5:1 to 3.0:1.

The reactor effluent at 30 is then quenched directly or indirectly as indicated at 31 in FIG. 1, to recover the heat at 31a and to remove heavy ends by-products indicated at 32 (two ring aromatics such as $C_8H_8$ and $C_{10}H_{10}$ and fuel oils). The cooled effluent at 33 is then fed to hydrogen chloride recovery processor 34 to remove hydrogen chloride from the gas stream. The recovered hydrogen chloride can be either as gas or as in hydrochloric acid. Such hydrogen chloride is fed at 35 to converter 36 and converted to chlorine, as for example in an electrolysis system or in a process using Deacon chemistry or the like. The Deacon chemistry is described in the following reaction:

$$2HCl + \tfrac{1}{2}O_2 \rightarrow Cl_2 + H_2O \qquad (3)$$

The recovered chlorine gas is used as feed at 37 to the methane chlorination reactor 16. The process gas, after the removal of hydrogen chloride, is fed at 38 to gas separators indicated at 39. During these separation processes, unreacted methane is separated for recycle at 40 to the methane chlorination reactor. Acetylene is converted to vinyl chloride 41 by reacting with hydrogen chloride, or to ethylene at 42 by hydrogenation techniques. Both ethylene produced from methane directly, and ethylene obtained from hydrogenation, are combined as a usable or salable product. Vinyl chloride is also recovered in a separation process as another salable product. Other products include hydrogen at 43 and light hydrocarbons and fuel gas, at 44. These include propylene, butylene, pantene, and aromatics (B, T, X). The exact process flow sheet depends on the specification of desired products.

EXAMPLES

The following examples illustrate the novelty and utility of the method:

EXAMPLE 1

Natural gas and chlorine are fed to the reactor at stoichiometric ratio. The inlet temperature of the reactant is 1027° C. The reactor pressure is 3 atm. The reactor inlet and effluent compositions are given in Table 1.

EXAMPLE 2

Natural gas and chlorine are fed to the reactor at methane to chlorine molar ratio equal to two. The reaction inlet temperature is 1177° C. The reactor pressure is 3 atm. The reactor inlet and effluent compositions are given in Table 2.

EXAMPLE 3

Natural gas and chlorine are fed to the reactor at 1427° C. The reactor pressure is 3 atm. The reactor inlet and outlet compositions are given in Table 3.

EXAMPLE 4

Natural gas and chlorine are fed to the reactor at 1427° C. The reactor pressure is 3 atm. The reactor inlet and outlet compositions are given in Table 4.

All of these examples show $C_2$ species as the primary product from methane by methane chlorination reaction. The ratio between acetylene and ethylene depends on the reaction temperature and methane-to-chlorine ratio.

TABLE 1

| | | |
|---|---|---|
| Inlet Temperature: | 1027° C. | |
| Reactor Pressure: | 3 atm-absolute | |
| $CH_4/Cl_2$ Molar Ratio: | 1 | |
| | wt % | Carbon Selectivity % |
| Reactants | | |
| $Cl_2$ | 81.55 | |
| $CH_4$ | 18.45 | |
| Products | | |
| $H_2$ | 0.55 | |
| HCl | 83.84 | |
| $CH_4$ | 3.24 | |
| $C_2H_2$ | 8.92 | 72.3 |
| $C_2H_4$ | 0.32 | 2.4 |
| $CH_2Cl_2$ | 0.01 | |
| $C_2H_3Cl$ | 0.03 | 0.1 |
| $C_4H_4$ | 0.06 | |
| $C_6H_6$ | 0.15 | 1.22 |
| $C_7$–$C_9$ Aromatics | 1.05 | |
| $C_{10}+$ | 1.83 | |
| | 100.00 | |

Ultimate $C_2$ Yield =
$$\frac{\text{wt \% of } C_2H_2 + C_2H_4}{\text{wt \% of } CH_4 \text{ in feed} - \text{wt \% of } CH_4 \text{ in product}} = 60.75\%$$

Carbon Selectivity =
$$\frac{\text{Total g-atom of carbon in component i}}{\text{Total g-atom of carbon from converted } CH_4} \times 100\%$$

TABLE 2

| | | |
|---|---|---|
| Inlet Temperature | 1177° C. | |
| Reactor Pressure | 3 atm-absolute | |
| $CH_4/Cl_2$ Molar Ratio | 2 | |
| | wt % | Carbon Selectivity % |
| Reactants | | |
| $Cl_2$ | 68.84 | |
| $CH_4$ | 31.16 | |
| Products | | |
| $H_2$ | 0.65 | |
| HCl | 70.64 | |
| $CH_4$ | 16.88 | |
| $CH_2Cl_2$ | 0.16 | |
| $C_2H_2$ | 9.63 | 83.16 |
| $C_2H_4$ | 0.99 | 7.93 |
| $C_2H_3Cl$ | 0.04 | 0.1 |
| $C_3H_6$ | 0.13 | 1.62 |
| $C_4H_4$ | 0.16 | |
| $C_4H_6$ | 0.01 | |
| $C_6H_6$ | 0.25 | 2.16 |
| $C_7$–$C_9$ | 0.37 | |
| $C_{10}+$ | 0.09 | |
| | 100.00 | |

TABLE 2-continued

Ultimate $C_2$ Yield = 74.11%

TABLE 3

| | | |
|---|---|---|
| Inlet Temperature | 1427° C. | |
| Reactor Pressure | 3 atm-absolute | |
| $CH_4/Cl_2$ Molar Ratio | 2 | |
| | Wt % | Carbon Selectivity % |
| Reactants | | |
| $Cl_2$ | 68.76 | |
| $CH_4$ | 31.24 | |
| | 100.00 | |
| Products | | |
| $H_2$ | 0.73 | |
| HCl | 70.49 | |
| $CH_4$ | 16.87 | |
| $CH_2Cl_2$ | 0.23 | |
| $C_2H_2$ | 11.21 | 96.22 |
| $C_2H_4$ | 0.34 | 2.14 |
| $C_2H_3Cl$ | 0.02 | 0.06 |
| $C_3H_6$ | 0.04 | 0.38 |
| $C_4H_4$ | 0.05 | |
| $C_6H_6$ | 0.01 | |
| $C_7$–$C_9$ | 0.01 | |
| | 100.00 | |

Ultimate $C_2$ Yield = 80.26%

TABLE 4

| | | |
|---|---|---|
| Inlet Temperature | 1427° C. | |
| Reactor Pressure | 3 atm-absolute | |
| $CH_4Cl$ Molar Ratio | 3 | |
| | Wt % | Carbon Selectivity % |
| Reactants | | |
| $Cl_2$ | 59.57 | |
| $CH_4$ | 40.43 | |
| | 100.00 | |
| Products | | |
| $H_2$ | 0.76 | |
| HCl | 61.16 | |
| $CH_4$ | 27.24 | |
| $CH_2Cl_2$ | 0.10 | |
| $C_2H_2$ | 10.23 | 95.79 |
| $C_2H_4$ | 0.37 | 3.05 |
| $C_3H_6$ | 0.07 | 0.57 |
| $C_4H_4$ | 0.04 | |
| $C_6H_6$ | 0.01 | |
| $C_7$–$C_9$ | 0.02 | |
| | 100.00 | |

Ultimate $C_2$ Yield = 80.4%

A typical design of a methane chlorination reactor couple is shown in FIG. 4. Each reactor couple consists of two columns 60 containing regenerative heat exchanger beds which are separated by void space 61 at the top of the beds to provide sufficient residence time for the reaction to occur. In the first bed 25a of FIG. 4, the temperature of the feed, i.e. natural gas and chlorine, is raised to the initial reaction temperature, 950°–1200° C., in the regenerative bed. The feed gases can be premixed in the first bed or segregated. In the case of segregated feeds, a partition is used to separate the feed gases. The methane chlorination reaction takes place in the void space 61, and transfer line 62, and after the reaction is completed, the reaction production mix passes to the top of the second regenerative bed at the reaction temperature, from about 1090°–1150° C., to about 720° C. The final heat exchanger temperature at 720° C. is chosen to avoid tar compound condensation in the bed.

The typical construction of the reactor is shown in FIG. 3, as referred to above. Each reactor couple consists of two identical beds. Each bed is enclosed by metal shell and ceramic type linings. The typical material used for the metal shell 20 is a high-performance heat-resistant alloy. High nickel containing alloys such as Ni-16Cr-2.5Fe-4.5Al-Y are resistant to oxidation and chlorine attacks at high temperature (>900° C.). These types of materials are preferred for the metal shell, which provides vessel strength and confinement of the reactants and products in the system. The ceramic lining material confines the thermal energy of gases in the reactor and prevents direct contact of corrosive gases to the metal shell. The heat exchanger beds consist of high temperature extra-high alumina balls. Typical composition of extra-high alumina can be found in Perry's Chemical Engineering Handbook (P. 23–73 of 5th Edition).

This material provides high fusion temperature (>1700° C.), excellent resistance to deformation during heating and cooling cycles, low permeability, excellent heat strength, good resistance to thermal shock and good resistance to acids. The diameters of the balls is about 0.1 to 5.0 inches which is determined by the required gas-solid heat transfer surface area and by the gas velocity flowing through the bed void. The alumina balls release heat to the reactant gases in preheating cycle and absorb heat from the reaction products in cooling cycle.

The operation of each coupled reactor is cyclical. At the start-up of reactor operation, the first regenerative heat exchanger bed 25a is preheated until the top of the exchanger bed reaches about 1025° C. The feed mixture is fed through this preheated first bed and absorbs heat from the bed, then at 62 to the second vessel to flow downwardly through bed 125a and to exit at 70. At the same time, the temperature at the top of second regenerative heat exchanger bed is increased from 975° C., which is at the beginning of the cycle, to the preferred upper limit absorbing the heat from the reaction products at 1025° C., for example, by cooling the effluent. When the temperature at the top of the first regenerative heat exchanger bed 25a decreases to about 975° C. the flow is reversed, i.e. first to regenerative heat exchange bed 125a and then downwardly via bed 25a to exit at 71. When the flow is reversed, the feed is preheated in the second regenerative heat exchanger bed and the effluent is cooled in the first regenerative heat exchanger bed, 25a. Control valves for such flow reversing appear at 64–67, and may be operated as by a batch sequencer 68. The cycling is phased so that a substantially uniform composition of the combined effluent from the reactor vessel is obtained.

The block valves 64–47 are located outside the reactor and are operated at moderate temperatures compared to the high temperatures of the reaction zone.

The reactor temperature is controlled either by preheating the feed outside the reactor or by changing the cycle frequency. Changing the preheating of feed affects the temperature at the beginning and the end of the cycle. On the other hand, changing the cycle frequency affects the temperature at the end of the cycle.

As an example, 490 lb-moles/hr of methane and 246 lb-moles/hr of chlorine are premixed and preheated to 250° C. The premixed and preheated gases are fed to the methane chlorination reactor. As shown in FIG. 4, the temperature of the premixed feed is raised from 250° C. to the initial reaction temperature, 950°–1000° C. in the first heat regenerative exchanger bed 25a. The reactor effluent is then cooled in the second heat regenerative exchanger bed 125a from the reaction temperature (1090°–1150° C.) to about 720° C. The final heat exchanger temperature of the second regenerative bed at 720° C. is such as to avoid tar compound condensation in the bed.

The residence time of the gas in the reaction zone 61 and transfer line 62 is about 0.25 seconds. The void volume in each reactor couple is 1.7 m$^3$. The internal diameter of the reactor is 0.76 m. The total height of the reactor vessel is 7.2 m. For this example, three parallel reactor couples or pairs were employed.

Preheating of feed mixture from 250° C. to the average reactor inlet temperature at 975° C. requires 7,268,000 Kcal/hr. This heat is transfered from the alumina packing of the regenerative bed to the gas. Cooling of the reactor effluent from the average reactor outlet temperature of 1075° C. to the outlet of the regenerative bed requires removal of 7,268,000 Kcal/hr. This amount of energy is transferred from the gas to the alumina balls. In the next cycle, heat transfer is reversed. By operating in the cyclical mode, no external heat input or removal is required for the reactor. Should there be coke or tar build-up in the regenerative bed, air or oxygen can be introduced to burn-off the carbonacious materials.

FIG. 3 is labeled to show elements of a complete ethylene and vinyl chloride polymer production plant. It corresponds to FIG. 1, and also shows successive separations of reaction products as designated.

We claim:

1. The method for converting methane into at least one higher molecular weight hydrocarbon, which comprises reacting in a reaction zone a mixture of chlorine and a gas comprising methane in a mole ratio of methane to chlorine of about 1.5:1 to 5:1 under conditions to provide a reaction pressure of about 3 atmospheres and a reaction temperature of at least about 1,100° C., and to form as mixed reaction products hydrogen chloride and a hydrocarbon or hydrocarbons selected from the group that includes ethane, ethylene, acetylene, propylene and hydrogen, the methane and chlorine being introduced to said zone as feed, and pre-heating the feed by contact with hot, inert packing material and to a temperature or temperatures between about 900° C. and about 1,200° C., controlling feed pressurization to maintain said reaction pressure and including controlling the feed of methane and chlorine to said zone to achieve an exothermic reaction of the pre-heated methane and chlorine in the reaction zone to produce temperatures therein between 1,100° C. and 1,500° C.

2. The method of claim 1 including the step of mixing the methane and chlorine prior to feeding them into the reaction zone.

3. The method of claim 1 including separately feeding the methane and chlorine, as gases into the reaction zone.

4. The method of claim 1 including removing contaminants from the methane feed, prior to its introduction into the reaction zone.

5. The method of claim 1 wherein the molar ratio range of methane to chlorine is 1.5:1 to 5:1.

6. The method of claim 1 wherein the preferred molar ratio range of methane to chlorine is 1.5:1 to 3.0:1.

7. The method of claim 1 wherein said reaction products include hydrogen chloride, and including the steps of separating hydrogen chloride from said reaction products, recovering chlorine from the separated hydrogen chloridde, and re-cycling the recovered chlorine to the methane chlorination reaction zone.

8. The method of claim 1 wherein said reaction products include methane, and including the steps of separating methane from the reaction products, and re-cycling the recovered methane to the methane chlorination reaction zone.

9. The method of claim 1 wherein said reaction is carried out in an exothermic reaction zone and including controlling the rate of flow of methane and chlorine to said zone to control the temperature of said zone.

10. The method of claim 1 including flowing the methane and chlorine into a first regenerative heat exchanger zone which contains an inert material and wherein reactants are preheated by absorbing heat from the packing material in the first regenerative heat exchanger zone, and flowing the reactant mix into a reaction zone and wherein reaction products are exothermically produced and then flowing the reaction products to a second regenerative heat exchanger zone containing inert material to transfer heat to the inert material in said second zone.

11. The method of claim 10 including reversing the flow of the methane and chlorine to flow same to the second zone wherein reaction products are produced, exothermically, and then flowing the reaction products to the first reaction zone to transfer heat to the inert material therein.

12. The method of claim 10 wherein said inert material comprises alumina balls.

* * * * *